United States Patent [19]

Guadagno

[11] Patent Number: 5,106,472
[45] Date of Patent: Apr. 21, 1992

[54] ELECTROPHORESIS GEL LAYER INTERFACE
[75] Inventor: Philip A. Guadagno, Vidor, Tex.
[73] Assignee: Helena Laboratories Corporation, Beaumont, Tex.
[21] Appl. No.: 426,277
[22] Filed: Oct. 25, 1989

Related U.S. Application Data
[63] Continuation of Ser. No. 254,087, Oct. 6, 1988, abandoned.
[51] Int. Cl.[5] ............................ G01N 27/26; B01D 57/02
[52] U.S. Cl. ............................... 204/299 R; 204/182.8
[58] Field of Search ............... 204/299 R, 182.8, 180.1

[56] References Cited
U.S. PATENT DOCUMENTS

| 3,402,118 | 9/1968 | Mutter | 204/299 R |
|---|---|---|---|
| 3,674,678 | 7/1972 | Post, Jr. | 204/299 R |
| 3,677,930 | 7/1972 | Meshbare et al. | 204/299 R |
| 3,773,646 | 11/1973 | Mandle | 204/299 R |
| 4,576,693 | 3/1986 | Kreisher et al. | 204/299 R X |
| 4,624,768 | 11/1986 | Yoshida et al. | 204/299 R |
| 4,892,639 | 1/1990 | Sarrine | 204/299 R |

FOREIGN PATENT DOCUMENTS 8704948  9/1987  PCT Int'l Appl.
8900689  1/1989  PCT Int'l Appl.

Primary Examiner—John Niebling
Assistant Examiner—John S. Starsiak, Jr.
Attorney, Agent, or Firm—Spencer & Frank

[57] ABSTRACT

A thermally conductive, electrically insulating interface adapted to be interposed between the heat conductive metal floor of an electrophoresis chamber and an electrophoresis plate for conducting heat from the plate to the chamber floor. The interface is preferably silicone or a silicone base, and demonstrates a preferential affinity to the electrophoresis plate. Optionally a support layer or backing layer may be included as part of the interface member.

19 Claims, 1 Drawing Sheet

5,106,472

ELECTROPHORESIS GEL LAYER INTERFACE

This application is a continuation of application Ser. No. 07/254,087, filed Oct. 6, 1988, now abandoned.

BACKGROUND OF THE INVENTION

This invention relates to an apparatus for electrophoresis and, more particularly, to an improved gel layer interface adapted to be interposed between the floor of an electrophoresis chamber and an electrophoresis plate.

Electrophoresis is a well-known technique for separation of protein fractions under the influence of an electric field. The material to be electrophoresed is placed on a gel which may be agarose gel cast on a substrate. Typical substrates commonly used are Mylar, a DuPont trademark for a polyester film and Lexan, a General Electric trademark for a polycarbonate film. Among the parameters to be considered during electrophoresis are voltage, amperage, heat and time. As voltage is increased between opposite ends of the electrophoresis gel, the electrophoretic velocity of movement is increased proportionately. However, absent other changes in parameters, the heat increase resulting from a voltage increase becomes a limiting factor. The mobility of the proteins is increased as temperature increases but the proteins are easily denatured and care must be taken generally not to exceed 50° C. Higher temperatures lead to greater evaporation, which increases the ionic strength and, higher temperatures also increase buffer movement thereby tending to deplete a buffer reservoir. Longer running time merely increases the opportunity for problems such as excessive heat and buffer depletion.

When electrophoresis is performed within a chamber such as the REP System marketed by Helena Laboratories Corporation of Beaumont, Tex., the assignee of the present application, the floor or bottom of the electrophoresis chamber is typically made of metal which is both a thermal conductor and an electrical conductor. The electrophoresis plate, e.g., the gel cast on the substrate, is placed on the metal chamber floor, the sample is placed on the gel, and the sample is subjected to the voltage gradient and elevated temperature.

DESCRIPTION OF THE PRIOR ART

The REP system, while providing faster electrophoresis, utilizes greater voltage gradients and thus results in more heat being generated. It may be appreciated that the electrophoresis chamber floor functions as a cooling mechanism based upon the Peltier principle to withdraw heat from the electrophoresis plate. In this way, proteins may be electrophoresed at higher voltages without the resultant adverse effects of higher temperatures. But, since the chamber floor is metal, an interface must be provided between the chamber floor and the electrophoresis plate, otherwise there is a risk of a "short circuit", i.e., an electrical path from one electrode, through the chamber floor, to the other electrode, thus bypassing the electrophoresis plate. In the past, deionized water was used as such an interface since deionized water had sufficient dielectric strength to avoid these short circuits. This necessitated the application of deionized water onto the metal chamber floor prior to the placement of the electrophoresis plate on the floor; a procedure which had to be repeated each time a new plate was to be subjected to electrophoresis. In addition to being slow, cumbersome and untidy, when water was used air bubbles were often present and when the electrophoresis plate was placed on top of the water, dry spots or hot spots occurred over the air bubbles causing hot spots or burning on the electrophoresis plate. These hot spots, or burning, frequently destroyed the electrophoresis pattern.

A subsequent approach to the problems caused by the use of deionized water was the provision of a removable covering on the chamber floor to function as an interface between the chamber floor and the electrophoresis plate. A fluorosurfactant was utilized such as Zonyl FSO, a DuPont trademark for perfluoroalkyl ethoxylate, and even a fiberglass reinforced Teflon covering was also utilized. Teflon has a high dielectric strength and provided sufficient electrical insulation and was used with the fluorosurfactant. However, these coatings or coverings used with fluorosurfactants were also slow, cumbersome and untidy but were preferable to deionized water insofar as reducing the air bubble problem. However, this type of covering or coating had to be replaced, in its entirety, if a single scratch or small damage spot occurred and the fluorosurfactant was required as an additional interface between the covering or coating and the electrophoresis plate.

Hence the present invention is directed to the problem of a convenient, inexpensive, easily replaceable gel plate interface to be positioned between the electrophoresis metal chamber floor and the electrophoresis plate.

SUMMARY OF THE INVENTION

The present invention overcomes the aforementioned disadvantages and problems by providing an easily removable, easily replaceable, high dielectric, thermally conductive gel layer interface adapted to be placed between the metal electrophoresis chamber floor and the electrophoresis plate. The present invention relates, preferably, to a silicone based gel layer interface which provides numerous advantages and certain unexpected advantages as compared to the gel layer interface member heretofore used.

BRIEF DESCRIPTION OF THE DRAWINGS

The various benefits and advantages of the present invention, together with other objects which may be attained by its use, will become more apparent upon reading the following detailed description of the invention taken in conjunction with the drawings.

In the drawings, wherein like reference numerals identify corresponding parts.

DETAILED DESCRIPTION OF THE PRESENT INVENTION

Figure 1:
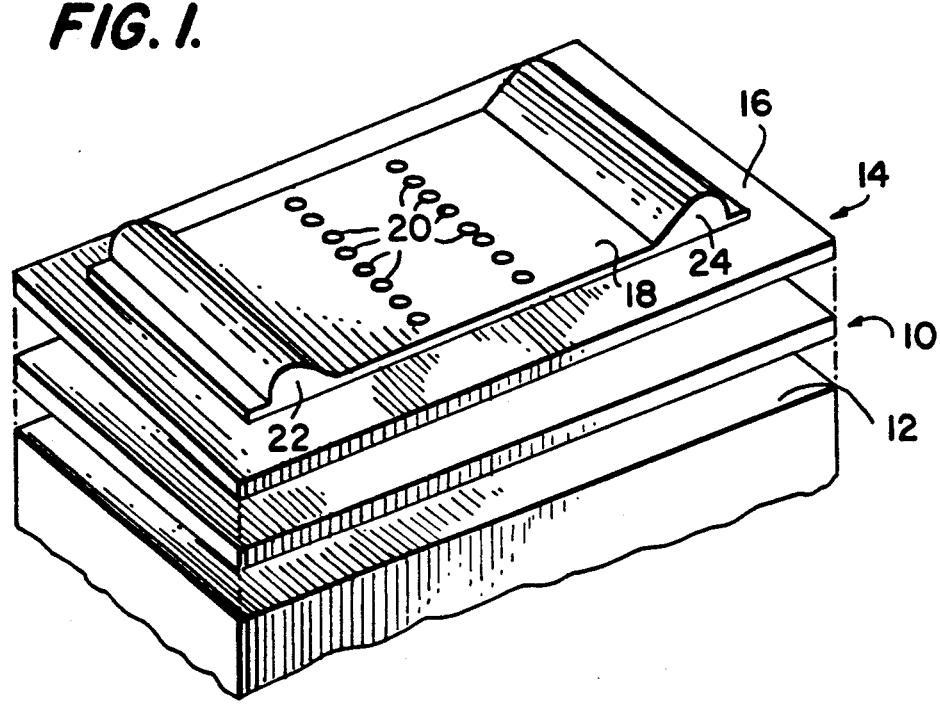
FIG. 1 is an exploded, perspective diagrammatic illustration of an electrophoresis plate, an interface member according to the principles of the present invention, and an electrophoresis chamber floor.

With reference to the drawings, an interface member 10 is illustrated in FIG. 1 interposed between a floor 12 and an electrophoresis plate 14. The floor 12 is, as previously described, a metal floor of an electrophoresis chamber and is intended to function as a Peltier cooling mechanism for withdrawing heat from the electrophoresis plate. The electrophoresis plate 14 may be considered as including a substrate 16 of Mylar or Lexan to which is adhered a gel layer 18. The gel layer 18 may, for the purpose of illustration and explanation, be considered as an agarose gel layer having a series of wells or depressions 20 for application of samples or specimens. The opposite ends 22, 24 of the gel layer are enlarged and function as buffer reservoirs. The details of the interface member 10 will be explained in greater detail with reference to the embodiment of FIG. 2.

Figure 2:
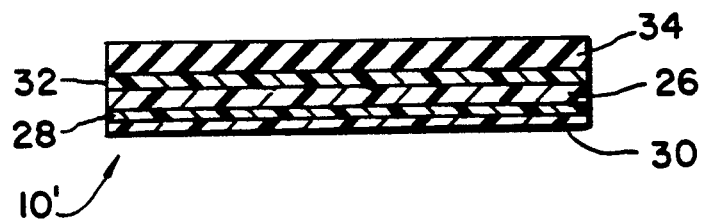
FIG. 2 is a sectional elevation view of another form of interface member according to the principles of the present invention.

Referring next to FIG. 2, an interface member 10' is illustrated in a form in which it may be stored prior to use. The interface member 10' as illustrated in FIG. 2 includes a plurality of layers, it being understood that some of the layers are provided for convenience in shipment or storage and are intended to be removed prior to placement of the interface member 10' between the metal electrophoresis chamber floor and the electrophoresis plate.

The interface member 10' as illustrated is a generally large, rectangular flat multi-layer member including a first support layer 26. Layer 26 is generally flat, rectangular and has opposed sides or faces. The support layer 26 may be a polyester film such as a Mylar film, Mylar being a DuPont trademark for a polyester film, the support layer 26 having a thickness of about 0.001–0.002 inches. One side of the support layer 26 is provided with an adhesive 28 which may preferably be an acrylic adhesive layer and this adhesive layer 28 is covered with a backing layer 30 which may be a backing paper or release paper which may be conveniently removed from the adhesive layer such as by grasping one corner of the backing layer 30 and peeling the backing layer from the adhesive layer. This type of backing layer or release paper is well-known and, in fact, DuPont Mylar may even be purchased with an acrylic adhesive and backing layer secured thereto. Since the acrylic adhesive is polar, the backing layer 30 should be non-polar or have a non-polar surface in contact with the adhesive. Hence a polyolefin sheet or polyolefin coated paper is typically used as a backing layer.

The interface 10' according to the principles of the present invention may also include an adhesive 32, such as an acrylic adhesive, on the opposite side or face of the support layer 26 from the first adhesive 28. Thus adhesive 28 and adhesive 32 are on the opposite generally flat surfaces of the support layer 26. A removable backing paper or release paper, not shown, may be placed over the adhesive 32. Mylar brand polyester film may be purchased in sheet form with adhesive on both sides of the sheet and with backing paper covering the adhesives on either side of the film.

According to the principles of this embodiment of the present invention, in addition to the high dielectric strength of the support layer, the interface 10' includes a high dielectric material such as silicone or a silicone-based compound. Silicone has certain benefits such a reduced surface tension, between the substrate plate, high dielectric strength and when of the proper thickness, adequate thermal conductivity and provides a surprising, unexpected benefit as will hereafter be described.

According to the principles of the present invention, the upper backing layer (not shown) is removed from the support layer 26 and a silicone layer 34 is applied on the support layer. The silicone layer 34 is preferably about 0.005–0.008 inches thick. The silicone layer may be referred to as the layer which contacts the electrophoresis plate while the support layer 28 may be thought of as the layer which contacts the metal electrophoresis chamber floor. Thus to utilize the interface member 10' according to the principles of the present invention, the backing layer 30 is removed and the resulting interface member 10' is positioned between the metal electrophoresis chamber floor and the electrophoresis plate. Adhesive layer 28 provides positive adherence between the metal chamber floor and the interface member 10' and provides for more uniform contact than through the use of water or fluorosurfactants. The silicone layer 34 is in contact with the electrophoresis plate (and more particularly with the substrate 16 of the electrophoresis plate) and, a surprising result has been demonstrated, namely, that the silicone has demonstrated a preferential affinity toward the electrophoresis plate substrate 16. The nature of this affinity is not completely understood but a uniform contact between the electrophoresis plate 14 and the plate-facing layer 34 occurs thus providing for uniform cooling of the electrophoresis plate. At the conclusion of the electrophoresis, the electrophoresis plate 14 may be easily removed from the interface member 10' by grasping a corner of the electrophoresis plate 14 and lifting or peeling the plate from the interface member without adversely affecting the electrophoresis protein fraction resolution. Similarly, when it is necessary or desirable to replace the interface member, the interface member may be easily removed from the metal floor 12 by grasping a corner of the interface member and peeling the interface member from the metal chamber floor 12 by easily overcoming the adhesive nature of the layer 28.

Figure 3:
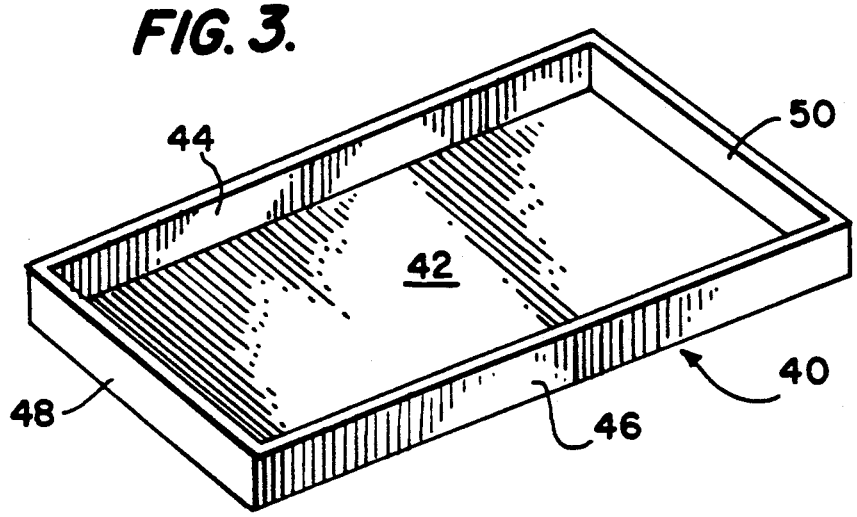
FIG. 3 is a diagrammatic illustration of a mold for making an interface member according to the principles of the present invention.

With reference to FIG. 3, a method of manufacture of the interface member 10' according to the principles of the present invention will now be described. It is convenient and, in fact, preferable to start with a large rectangular support layer 26 having adhesive on both sides and backing layers on both sides as previously described. The sheet may be placed in a mold 40 which is a generally rectangular mold having a flat mold floor 42, a pair of opposed upwardly extending mold side walls 44, 46 and a pair of opposed upwardly extending mold end walls 48, 50. The floor, side walls and end walls define a mold cavity into which the support layer is placed with the backing layer 30 in contact with the mold floor 42. The upper backing layer (not shown) may be removed and then the electrophoresis plate-facing layer 34 placed into the mold cavity. A room temperature vulcanizing silicone, such as the type commonly marketed as Dow Corning 100% Silicone Rubber, is poured into the mold and any excess may be screed with a knife edge or the like such that there is a 0.005–0.008 inch thick layer of silicone on the support layer 26. The silicone vulcanizes or cures, at room temperature, and may then be removed from the mold.

According to the principles of the present invention, it may be appreciated that other support layers 26 may be utilized and other high dielectric layers or plate-facing layers 34 may be utilized.

According to the principles of the present invention, referring back to FIG. 1, the interface member 10 may be a thin silicone layer without any additional support layers 26. A thin silicone layer may even be placed on the electrophoresis plate itself.

As yet another alternative, a thin silicone member may be employed with adhesive and with removable backing layers 30. The adhesive need not be provided as part of the interface member but may be separately applied (e.g., in the form of a spray) onto the metal chamber floor just prior to placing the interface member thereon.

Hence the present invention requires a material and a high thermal conductivity, which will not burn or be damaged at the electrophoresis temperature and voltage gradient, and a high dielectric constant, as the interface between the chamber floor and the conventional electrophoresis plate.

It is within the scope of the present invention that silicones other than room temperature vulcanizing silicones may be utilized; thermoset silicones ma be injection molded into a closed mold or cast onto a support layer and cured. Production of the interface 10 may be by extrusion with subsequent adhesive (if desired) being thereafter placed directly on the interface.

Among the benefits of the present invention is the elimination of need for deionized water or additional liquid surface active interfacing agents between the metal chamber floor and the electrophoresis plate 14. The present invention permits high temperature electrophoresis without damage to the electrophoresis plate, or to the metal chamber floor and the present invention provides sufficient thermal conductivity such that proper cooling of the electrophoresis plate occurs, thus avoiding damage to the electrophoresis plate and damage to the specimens. The present invention provides not only a more uniform distribution of heat and a more uniform conductance of heat from the electrophoresis plate to the metal chamber floor but also avoids potential problems which occurred during the use of liquid interfaces, namely, the presence of air bubbles which caused heat damage or burning to the electrophoresis plate, and electrical shorting of the plate through the liquid interface as it becomes contaminated with gel buffers during electrophoresis.

The foregoing is a description of a preferred embodiment of the present invention. Many changes and modifications may be made without departing from the spirit and scope of the present invention. The present invention, therefore, should be limited only by the following claims.

What is claimed is:

1. For an electrophoresis system of the type including a heat conductive floor and an electrophoresis plate, the improvement of interface means to be interposed between said electrophoresis plate and said heat conductive floor, said interface means comprising:
   a thin, generally flat multi-layered member, each layer having opposed first and second sides, the first side of a first layer for contacting the electrophoresis plate and the second side of a second layer for contacting the heat conductive floor;
   said first layer having sufficient dielectric strength for preventing an electrical short circuit between the electrophoresis plate and the heat conductive floor and further having sufficient thermal conductivity for conducting heat from said electrophoresis plate to said heat conductive floor;
   the second side of the first layer and the first side of the second layer being generally oriented in an opposing relationship.

2. The invention as defined in claim 1 wherein said first layer is a silicone sheet having a thickness from about 0.005 to about 0.010 inches.

3. The invention as defined in claim 1 wherein said first layer has a preferential affinity for the electrophoresis plate.

4. The invention as defined in claim 1 wherein said first layer includes silicone.

5. The invention as defined in claim 1 and further including adhesive means between said first and second layers.

6. The invention as defined in claim 5 and further including adhesive means on said second side of said second layer for releasably securing said second layer to said heat conductive floor.

7. The invention as defined in claim 1 wherein the heat conductive floor formed of metal.

8. The invention as defined in claim 1 wherein the heat conductive floor is an electrophoresis chamber floor.

9. The invention as defined in claim 1 wherein the heat conductive floor is a metal electrophoresis chamber floor.

10. An interface member adapted to be interposed between an electrophoresis plate and a metal floor comprising:
    a thin generally flat member having opposed first and second sides, the first side for contacting the electrophoresis plate and the second side for contacting the metal floor;
    said thin generally flat member having sufficient dielectric strength for preventing an electrical short circuit between the electrophoresis plate and the metal floor and further having sufficient thermal conductivity for conducting heat from said electrophoresis plate to said metal floor;
    said thin generally flat member comprising a plurality of layers in face-to-face contact, one of said layers being a silicone sheet having a thickness from about 0.005 to about 0.010 inches, and another of said layers being a support layer for contacting said metal floor.

11. The invention as defined in claim 10 wherein adhesive is provided intermediate said silicone sheet and said support layer.

12. The invention as defined in claim 10 wherein said support layer is selected from the group consisting of polyester film and polycarbonate film.

13. The invention as defined in claim 10 and further including adhesive means on the side of said support layer opposite to said silicone sheet for releasably securing said support layer to said metal floor.

14. The invention as defined in claim 10 wherein a metal floor is part of an electrophoresis system.

15. The invention as defined in claim 10 wherein said metal floor is part of an electrophoresis chamber.

16. In a method of electrophoresis wherein an electrophoresis plate and a metal floor are provided, the improvement comprising the steps of:
    providing a thermally conductive electrically insulating layer;
    providing a second layer on said thermally conductive electrically insulating layer; and
    positioning said thermally conductive electrically insulating layer and said second layer intermediate said electrophoresis plate and said metal floor, with said thermally conductive electrically insulating layer facing said electrophoresis plate and second layer facing said metal floor.

17. The invention as defined in claim 16, and further including providing adhesive on said second layer; and releasably securing said second layer to said metal floor.

18. The invention as defined in claim 16 wherein said thermally conductive electrically insulating layer includes silicone.

19. The invention as defined in claim 16 wherein said second layer is positioned facing an electrophoresis chamber floor.

* * * * *